US009470475B1

(12) United States Patent
Morris

(10) Patent No.: US 9,470,475 B1
(45) Date of Patent: Oct. 18, 2016

(54) CONCEALED GUN CARRY DEVICE

(71) Applicant: Jerry Lee Morris, Ringgold, GA (US)

(72) Inventor: Jerry Lee Morris, Ringgold, GA (US)

(*) Notice: Subject to any disclaimer, the term of this patent is extended or adjusted under 35 U.S.C. 154(b) by 0 days.

(21) Appl. No.: 15/001,437

(22) Filed: Jan. 20, 2016

Related U.S. Application Data

(60) Provisional application No. 62/125,381, filed on Jan. 20, 2015.

(51) Int. Cl.
*F41C 33/02* (2006.01)
*F41C 33/00* (2006.01)
*F41C 33/04* (2006.01)

(52) U.S. Cl.
CPC ........... *F41C 33/008* (2013.01); *F41C 33/048* (2013.01); *A45F 2200/0591* (2013.01); *F41C 33/0245* (2013.01); *F41C 33/041* (2013.01)

(58) Field of Classification Search
CPC   F41C 33/041; F41C 33/048; F41C 33/0245; A45F 2200/0591
USPC ............................... 224/587, 192, 917.5, 913
See application file for complete search history.

(56) References Cited

U.S. PATENT DOCUMENTS

| | | | | |
|---|---|---|---|---|
| 3,315,855 A | * | 4/1967 | Boone | A45F 5/02 224/255 |
| 3,796,358 A | * | 3/1974 | Grubb | F41A 17/02 224/255 |
| 4,412,397 A | * | 11/1983 | Bayn | F41A 17/74 42/70.11 |
| 4,741,465 A | * | 5/1988 | Johnson | F41C 33/0209 224/230 |
| 4,982,522 A | * | 1/1991 | Norton | F41C 33/00 224/220 |
| 5,215,237 A | * | 6/1993 | Wu | A45C 13/20 150/132 |
| 5,337,936 A | * | 8/1994 | Blum | A45C 1/04 224/240 |
| 5,412,959 A | * | 5/1995 | Bentley | E05B 67/003 42/66 |
| 5,806,739 A | * | 9/1998 | Wood | F41A 23/18 211/64 |
| 6,019,404 A | * | 2/2000 | Pasquale | F41A 17/44 224/150 |
| 6,722,073 B2 | * | 4/2004 | Cossio | F41A 35/04 124/41.1 |
| 6,796,072 B2 | * | 9/2004 | Barber | F41A 17/44 42/70.11 |
| 8,991,668 B2 | * | 3/2015 | Pylypiak | F41C 33/048 224/192 |
| 9,080,824 B2 | * | 7/2015 | Chudwin | F41A 17/44 |
| 2012/0285063 A1 | * | 11/2012 | Woodford | F41A 17/42 42/70.11 |

* cited by examiner

*Primary Examiner* — Justin Larson
(74) *Attorney, Agent, or Firm* — Stephen J. Stark; Miller & Martin PLLC

(57) ABSTRACT

A carry device provides a concealed carry configuration supporting a handgun against at a waistband of an article of clothing by directing a tube into a barrel of the handgun from which a loop extends to loop around an article of clothing, such as a belt, and then provide a loop end which attaches to a rear portion of the handgun thereby providing it in a secure manner until a time to draw or remove the gun arises.

20 Claims, 2 Drawing Sheets

CONCEALED GUN CARRY DEVICE

CLAIM OF PRIORITY

This application claims the benefit of U.S. Provisional Patent Application No. 62/125,381 filed Jan. 20, 2015, which is incorporated by reference herein in its entirety.

FIELD OF INVENTION

The present invention relates to a concealed carry device and more particularly to a device for use in supporting a handgun internal to a waistband of an article of clothing such as pants, shorts, skirts and the like, with the device preferably retaining the gun between the article of clothing and the person.

BACKGROUND OF THE INVENTION

In the prior art, holsters and carrying devices are known to be bulky and uncomfortable. They are also often somewhat constrictive when performing certain tasks.

Additionally most prior art holsters are sized and/or designed for specific handgun or guns. If one owns multiple guns, it is likely they will need multiple carrying devices.

While holsters can fill a need for many uses to carry handguns, there is believed to be a need for an improved carry device for at least some applications.

SUMMARY OF THE INVENTION

Accordingly, it is an object of many embodiments of the invention to provide an improved carrying device which is comfortable and easy to use.

It is a further object of many embodiments of the invention to provide a product that can eliminate a need for purchasing multiple carrying holsters or devices for use with a plurality of handgun designs.

It is an object of many embodiments the present invention to provide an improved concealed carry device.

Another object of the embodiment of the present invention is an improved device with handguns for use in securing those handguns internal to the waistband of a user bottomwear.

Accordingly, presently preferred embodiments of the invention holds a handgun securely in the waistband of an article of clothing while preferably allowing the freedom to walk, run, stand, set, exercise and work with maximum flexibility and minimum discomfort.

Unlike holsters and other IWB (inside the waistband) carrying devices that add weight and bulk, a bungee design of this invention adds almost no weight or bulk to your waistband. Embodiments of this invention do not require the user to buy oversize pants in order to be comfortable when carrying your handgun IWB.

Although for many embodiments one size does not fit all, however, two sizes will fit most handguns that are commonly used as concealed carry weapons.

In accordance with a presently preferred embodiment of the present invention, a concealed carry device provides a tube which is preferably received within the barrel of a gun. The tube preferably connects to at least one resilient cord if not a loop of resilient cords having a loop end which is directed around the belt of a user and then secures to a rear portion of the gun such as over the hammer, slide and/or grip safety, depending on the configuration of the gun. Thus the gun is then secured internal to the bottomwear with the concealed carry device.

Many embodiments of the invention provide an inside the waistband (IWB) handgun receiver made from plastic tubing and bungee cord. The bungee cord preferably loops around and attaches to a belt. The plastic tube can be inserted into the barrel of the handgun. The handgun is then pushed barrel first into your waistband (between the waistband and the user's body). The loop of the bungee cord can then be pulled up over and around the handgun holding it securely in place inside the waistband. Removing the loop from the gun allows a user to pull the gun out of the waistband free of the carry device for many embodiments.

BRIEF DESCRIPTION OF THE DRAWINGS

The particular features and advantages of the invention as well as other objects will become apparent from the following description taken in connection with the accompanying drawings in which.

DETAILED DESCRIPTION OF THE PREFERRED EMBODIMENT

Figure 1:
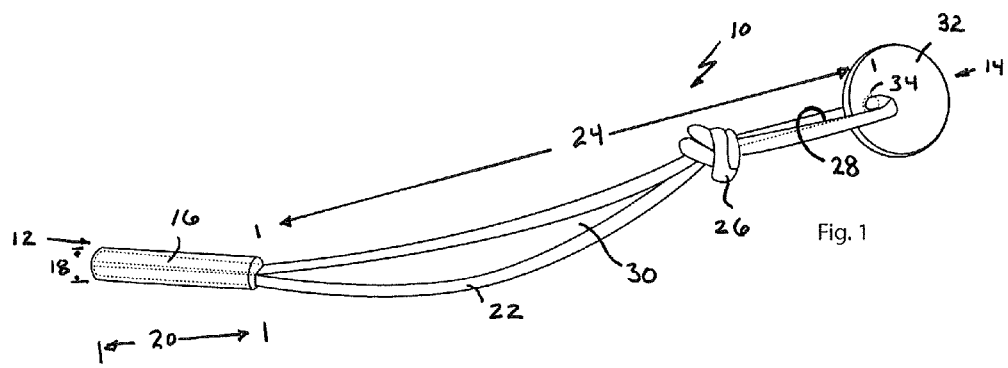
FIG. 1 is a side plan view of a presently preferred embodiment of the present invention before installation.

FIG. 1 shows carrying device 10 in an uninstalled configuration as presently provided by the manufacturer. The carrying device 10 has a first end 12 opposite of a second end 14. A tube 16 is further provided at the first end 12. The tube 16 is preferably at least a half inch or inch or inch and half, with the plastic tube 16 having a diameter preferably slightly smaller than the internal diameter of a barrel of the smallest handgun that the user will be using with the carrying device 10. For instance an 8 mm diameter 18 could be utilized for a .380 caliber handgun as well as larger caliber gun as a .45 caliber, etc. The exterior surface 40 of tube is preferably non-scratching or non-abrasive to barrels 38 of handguns 36. Plastic tubes 16 have been found satisfactory.

In addition to selecting an appropriate diameter 18 for the tube 16 the length 20 is preferably selected to be sufficient to retain the tube 16 within the barrel of a gun in an installed configurations as described in detail below. The application has discovered that a length 20 for many embodiments should be at least half an inch although one to about two inches or even more has been found preferable. A length 20 of 1.5 inches is a presently preferred length for many embodiments.

Connecting to the tube 16 is preferably a cord 22 which is preferably a resilient cord such as a bungee cord in the presently preferred embodiment. A length of the cord 20 from the end of the tube 16 to an end loop end of the bungee cord which forms a loop may be roughly eight inches as a length 24. Other embodiments can have other lengths 24.

The illustrated embodiment has a knot 26 which can form a loop end which will be discussed in further detail below.

In the preferred embodiment the stretchiness of the cord 22 is approximately capable of stretching a factor of slightly more than two so that when pulled to its limit of stretch it is roughly sixteen inches long. Other embodiments may have cords 22 of different resilience values and/or different lengths.

For at least some embodiments, we may be able to take the cord 22 and provide a knot 26 to create a small loop 28 particularly as compared to a large loop 30. Other embodiments may just have a single large loop 30 and no knot 26. It may be that for some embodiments the user forms the small loop 28. The small loop 28 can be utilized as a gripping point. Other embodiments may omit the small loop 28 and/or provide other devices for providing a gripping point or identification point such as a handle 32 which could be a coin having a hole 34 provided therethrough which receives the cord 22 therethrough during the manufacture one of the large loop 30 and/or small loop 28. Other handle 32 constructions other than small loop 28 or coin could be provided with still other embodiments or omitted for yet other embodiments entirely.

Figure 2:
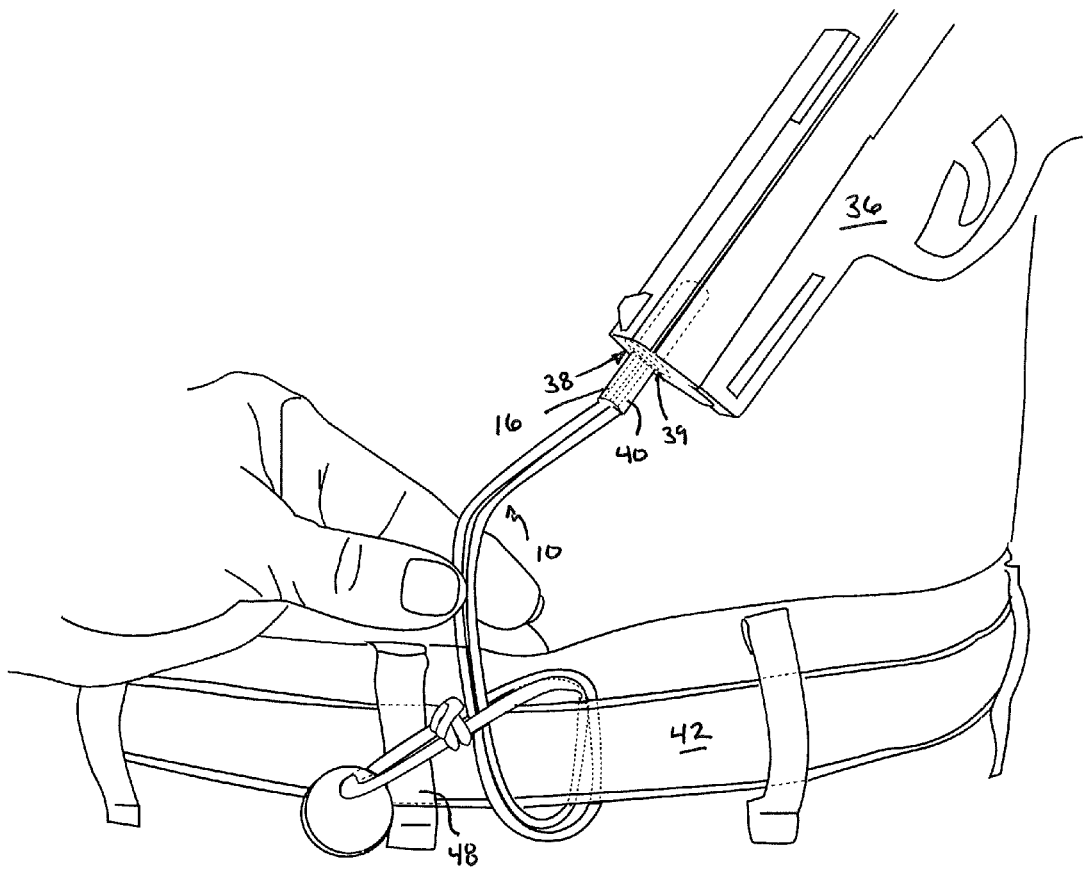
FIG. 2 is a side perspective view of the presently preferred embodiment of the present invention connected to a belt of a user with a portion of the product being inserted into the barrel of a handgun.
Figure 3:
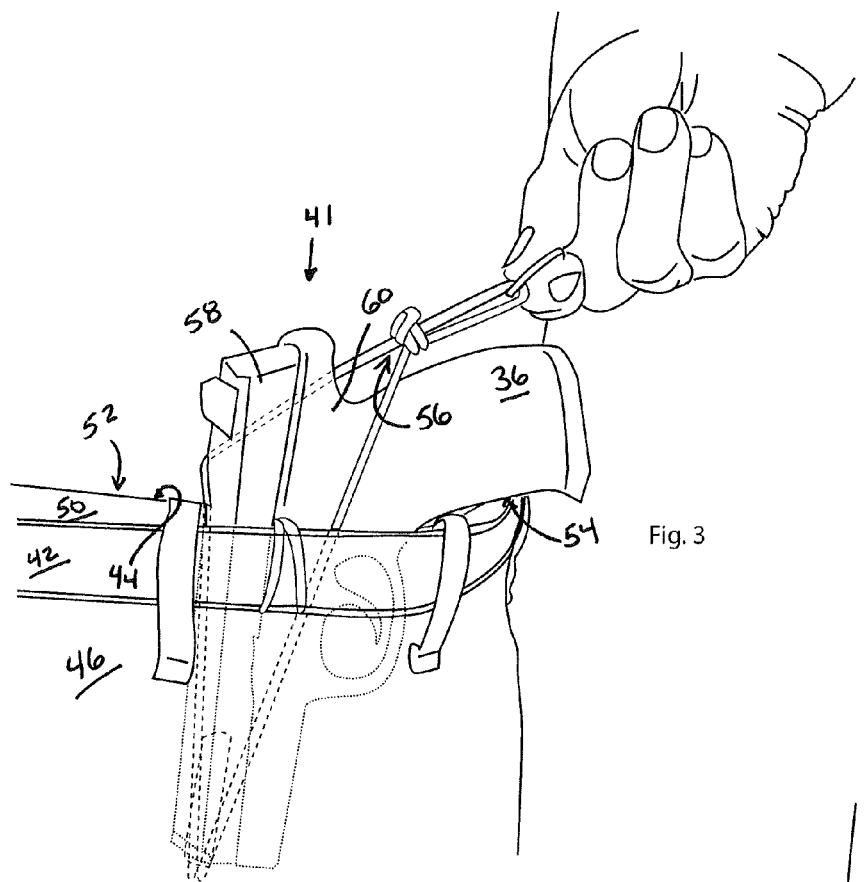
FIG. 3 is a side perspective view showing a handgun inserted into a waistband with the barrel pushed into the waistband of a user prior to securing an upper portion (or rear portion of the gun)

FIG. 2 shows an assembly step using the device 10 in FIG. 1 to provide an installed configuration with a handgun 36. Specifically the tube 16 is being shown inserted internal to barrel so as not to damage the internal surfaces of barrel 38 with a non-scratchy exterior surface 40. Additionally as discussed above, the exterior surface 40 of tube 16 provides a diameter 18 which is manufactured to be smaller than the caliber of the barrel 38. The embodiment discussed above with an 8 mm diameter 18 as compared to a .380 handgun, such a diameter would not work with a 22 caliber handgun. Instead, a smaller diameter 18 would be needed for such an embodiment as would be understood by those ordinarily skilled in the art. To provide an installed configuration, the tube 16 can start out below a belt 42 of a user with the top 14 above the belt 42.

Next one of the two ends either the top 14 or the bottom 12 can be inserted behind the belt 42 (or other closing portion) and then the tubing 16 can then pushed through the larger loop 30 so as to connect the large loop 30 of the cord 22 which can then be made smaller to connect to the belt 42 as shown to provide a "cow hitch." The tube 16 is at free end 12 up above the belt 42 and can be inserted into the barrel 38 at barrel outlet 39 of the gun 36. The resulting connection with the belt 42 is often referred to as a cow hitch or a lanyard hitch. The cow hitch could be either against the knot 26 in a snug configuration) or loose) or could be against the end 14 in a snug configuration (or loose) as is shown in FIG. 2 and as would be understood by those ordinarily skilled in the art.

Next the handgun 36 is directed internal to a waistband of the bottom wear worn by a user namely bottom wear 46 such as a pair of pants, shorts, skirt, etc. Furthermore, although the gun 36 is shown connected to a belt 42 it could also be connected to a belt loop 48 or other structure either on an exterior service 50 or on an internal surface 52 of the bottomwear 46 for at least some embodiments. The barrel of the gun 36 can then be directed into the waistband with a portion of the grip 54 possibly remaining external to the waistband 44 or for some embodiments being received internal to the waistband 44 (or both).

In order to complete the securing step, a loop end 56 which was formerly utilized to provide the cow hitch on the belt 42 and FIG. 2 can now be pulled up over a rear portion 41 of the handgun 36 (as opposite to the barrel outlet 39 such as over a slide 58 and/or hammer for an automatic as illustrated and possibly over the grip safety 60 so as to secure handgun 36 against the bottom wear 46 in the desired configuration preferably being secured to a belt 42 or other portion or possibly the outerwear 46 itself.

Figure 4:
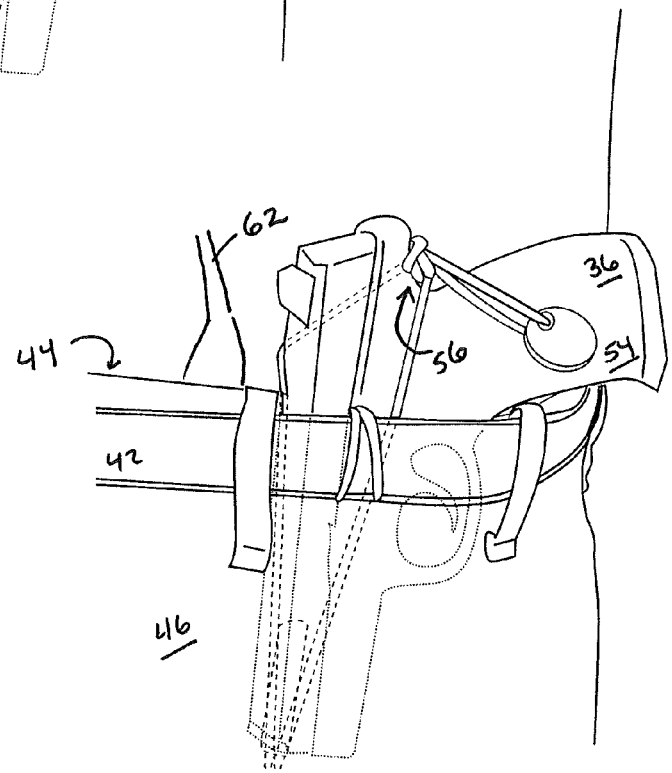
FIG. 4 is a side perspective viewing showing the tube internal to the barrel at one end of the handgun with the handgun secured to the belt of the user and the upper portion secured as well in a concealed carry configuration.

As illustrated by FIG. 4 the grip 54 is shown only slightly being sticking out of the waistband 44 and could either be internal or external with the waistband 44 as discussed above. Suspenders 62 may be useful to help then holding up the bottom wear 46 as well as for use by some parties. It is likely that the belt 42 would provide sufficient snugness to keep the bottom wear 46 from tending to sag for some embodiments.

While the illustrated figures show the use with a semi-automatic handgun, the same concept applies to a revolver with the loop end 56 being pulled over a hammer spur 59 or other portion so as to then rest against a frame or other portion of the pistol handgun 36. With the installation of FIG. 4 completed, the gun 36 is now in an installed configuration or a concealed carry position.

When someone desires to draw the handgun 36 or otherwise remove it such as at the end of the day, a user can often proceed with only one hand, and certainly with two, to push the loop end 56 over the hammer and/or slide depending on the configuration of the handgun 36 such as with one's thumb, possibly while holding the grip 54 with that hand and then pull the gun 36 straight up which will then release the tube 16 from the barrel 38 so that the gun 36 may either then be stored or fired. The handle 32, small loop 28 or other identifier may be utilized to assist a user finding the loop end 56, possibly without looking.

For emergency situations the gun 36 may be grabbed and pulled straight up without disengaging the loop end 56 first so that as the gun 36 is pulled up the tube 16 is pulled out of the barrel 38 and then the cord 22 then tends to unwrap from the belt 42 due to the resilient action of the cord 22 attempting to regain its non-stretched shape thereby allowing the user to point, aim and/or fire the handgun 36.

While for the present embodiment shows the small loop 28 it is equally possible that no small loop 28 is provided for other embodiments and just a large loop 30 is provided. Further, it is possible that the handle 32 such as the coin could be provided for some embodiments whether in the form of a coin as illustrated or otherwise. Still other detachment mechanisms may be utilized with other embodiments.

When assembling the device 10, it is possible to cut the cord 22 to a desired length as well as the tube 16 to a desired length which preferably has a hollow bore. The handle 32 can be inserted along the length 24 of the cord 22 and then the two ends of the cord pushed through the tube 16. The applicant then preferably applies an adhesive to the ends of a sufficient amount and then pulls the cord 22 back up into at least up to the bottom 12 of the tube 16 to then allow the adhesive to curl. With a little further processing the device 12 is then ready for packaging and sale for many embodiments. Other embodiments may be constructed differently.

While preferred embodiments use a loop of cord 22 it may be possible that other embodiments provide a carry device 10 having a tube 16 at a first end 12 as well as a resilient cord 22 connected to the tube 16 extending from the first end 12 towards the second end 14 opposite the first end 12 with a loop end such as either the end 16 or at the knot 26 as would be understood by those ordinarily skilled in the art. In such way the loop end at the knot 26 is at least approximate to the second end 16.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

The invention claimed is:

1. A method of concealed carrying a handgun comprising the steps of:
    a) providing a carry device having a tube at a first end and a resilient cord connected to the tube extending from the first end toward a second end opposite the first end with a loop end at least proximate to the second end;
    b) attaching the carry device to a user wearing a belt and an article of clothing having a waistband by directing the carry device between a portion of the article of clothing having the waistband and the belt and then forming a cow hitch against the belt with the loop end and with the tube directed upwardly above the bottom clothing;
    c) inserting the tube into a barrel of a handgun, said tube inserted into a barrel outlet;
    d) pushing the gun into the waistband opposite the portion of the article of clothing from the belt; and then
    e) pulling the loop end over a rear portion of the handgun opposite from the barrel outlet thereby securing the handgun in a concealed carry configuration.

2. The method of claim 1 wherein the article of clothing is selected from the group of pants, shorts and skirts.

3. The method of claim 1 wherein the tube has a length of at least about one inch.

4. The method of claim 1 wherein the cord forms a loop terminating at the loop end at the second end.

5. The method of claim 1 wherein the cord is connected to a handle located towards the second end, and further comprising the step of removing the handgun by:
    directing the loop end over the rear portion of the handgun and pulling the handgun out of the waistband thereby removing the tube from the barrel.

6. The method of claim 1 further comprising providing a handle connected to the cord, said handle disposed towards the loop end when in the concealed carry configuration.

7. The method of claim 6 wherein the cord is connected to a handle located towards the second end, and further comprising the step of removing the handgun by:
    directing the loop end over the rear portion of the handgun and pulling the handgun out of the waistband thereby removing the tube from the barrel.

8. The method of claim 7 wherein the handle is operated by the user to pull the loop end off of the handgun and then pulling the handgun out of the waistband of the user.

9. The method of claim 1 wherein the resilient cord has a stretch factor of at least about 2.

10. The method of claim 1 wherein the tube has a diameter of about 8 mm.

11. The method of claim 1 wherein the exterior surface of the tube has a non-scratching surface against metal.

12. A method of concealed carrying a handgun comprising the steps of:
    a) providing a carry device having a tube at a first end and a resilient cord connected to the tube extending from the first end toward a second end opposite the first end with a loop end at least proximate to the second end;
    b) attaching the carry device to a user wearing an article of clothing having a waistband by directing the carry device against a portion of the article of clothing having the waistband and forming a cow hitch adjacent to the article of clothing with the loop end and with the tube directed upwardly above the bottom clothing;
    c) inserting the tube into a barrel of a handgun, said tube inserted into a barrel outlet;
    d) pushing the gun into the waistband opposite the portion of the article of clothing from the belt; and then
    e) pulling the loop end over a rear portion of the handgun opposite from the barrel outlet thereby securing the handgun in a concealed carry configuration.

13. The method of claim 12 wherein the carry device is secured with the cow hitch to a belt.

14. The method of claim 12 wherein the article of clothing is selected from the group of pants, shorts and skirts.

15. The method of claim 12 wherein the tube has a length of at least about one inch.

16. The method of claim 12 wherein the cord forms a loop terminating at the loop end at the second end.

17. The method of claim 12 wherein the cord is connected to a handle located towards the second end, and further comprising the step of removing the handgun by:
    directing the loop end over the rear portion of the handgun and pulling the handgun out of the waistband thereby removing the tube from the barrel.

18. The method of claim 1 further comprising providing a handle connected to the cord, said handle disposed towards the loop end when in the concealed carry configuration.

19. The method of claim 18 wherein the cord is connected to a handle located towards the second end, and further comprising the step of removing the handgun by:
    directing the loop end over the rear portion of the handgun and pulling the handgun out of the waistband thereby removing the tube from the barrel.

20. The method of claim 19 wherein the handle is operated by the user to pull the loop end off of the handgun and then pulling the handgun out of the waistband of the user.

\* \* \* \* \*